United States Patent
Sturm

(10) Patent No.: US 6,377,652 B1
(45) Date of Patent: Apr. 23, 2002

(54) METHODS AND APPARATUS FOR DETERMINING MINERAL COMPONENTS IN SHEET MATERIAL

(75) Inventor: Steven Perry Sturm, Dublin, OH (US)

(73) Assignee: ABB Automation Inc., Columbus, OH (US)

( * ) Notice: Subject to any disclaimer, the term of this patent is extended or adjusted under 35 U.S.C. 154(b) by 0 days.

(21) Appl. No.: 09/477,956

(22) Filed: Jan. 5, 2000

(51) Int. Cl.[7] .............................................. G01N 23/06
(52) U.S. Cl. .......................... 378/53; 378/51; 378/157
(58) Field of Search ............................ 378/53, 51, 157, 378/156

(56) References Cited

U.S. PATENT DOCUMENTS

| | | | | |
|---|---|---|---|---|
| 3,435,220 A | * | 3/1969 | Hanken | 378/53 |
| 4,047,029 A | * | 9/1977 | Allport | 378/53 |
| RE30,884 E | * | 3/1982 | Buchnea | 378/53 |
| 4,696,023 A | * | 9/1987 | Kuusi | 378/53 |
| 5,778,041 A | | 7/1998 | Chase et al. | |
| 5,854,821 A | * | 12/1998 | Chase et al. | 378/53 |

FOREIGN PATENT DOCUMENTS

| EP | 0 394 128 A2 | 10/1990 |
|---|---|---|

* cited by examiner

*Primary Examiner*—Drew Dunn
(74) *Attorney, Agent, or Firm*—Stevens & Showalter LLP

(57) ABSTRACT

A method and system for on-line measurements of mineral additives in or on a paper web utilizing shaped spectrum x-rays and solid-state PIN detectors. Each of three detectors are cover by a filter used to shape the spectrums of x-rays received by the detectors. The filters are selected to maximize sensitivity differences between detectors for the desired detectable mineral additives. A computer processes signals from the detectors and from basis weight and moisture measuring instruments to determine total mineral content, and the individual amounts of mineral additives in or on (e.g. coating) the paper web.

26 Claims, 3 Drawing Sheets

METHODS AND APPARATUS FOR DETERMINING MINERAL COMPONENTS IN SHEET MATERIAL

BACKGROUND OF THE INVENTION

The present invention relates to a system and method for determining the mineral components in sheet material, and more particularly, for measuring the concentrations of individual components of mineral additives in a paper web in an on-line paper manufacturing process using a single x-ray source and multiple x-ray detectors, each detector with a different filter.

In addition to paper pulp fibers, paper manufactures use varying amounts of mineral additives, commonly referred to as "ash", to add strength, color and to change certain qualities like printability, opacity and brightness of their paper products. Such mineral additives include clay, kaolin, gypsum, calcium carbonate, barium sulfate, talc and titanium dioxide. As mineral additives are often cheaper than paper pulp, these inorganic materials are also used to lower manufacturing costs.

In present day paper manufacturing, clay, calcium carbonate and talc are commonly used mineral additives. While mineral additives have the above noted benefits, if too much mineral additive is used, i.e., if either the overall additive content exceeds an acceptable level or if any one of the components of these inorganic materials exceeds acceptable individual limits, the over-all quality and characteristics of the produced paper will be impaired. Additive limitations are particularly important to producers of cigarette paper who often use large quantities of titanium dioxide and calcium carbonate and have strict quality standards for their paper. Therefore, during the manufacturing process it is important to monitor and regulate both the total mineral additive content and the individual component concentrations of the mineral additives.

In the prior art, total mineral content has been determined by summing the measured individual component concentrations of the mineral additives present in the paper near the end of the paper making process. Either x-ray absorption or x-ray fluorescence have been employed to measure the individual component concentrations of the mineral additives. One or more measurement beams are directed through the continuously advancing paper web with each beam being received by a corresponding x-ray detector on the other side of the web. A computer, which receives signals representative of both the beam(s) and the detector(s), compares the signals and, using well-known or readily derived equations, computes the individual component concentrations of the mineral additives in the paper web.

Generally speaking, the gamma induced x-ray fluorescence approach for measuring total mineral content in paper is hampered by the following factors: low signal levels when counting photons; a slower count rate than the x-ray absorption method; it uses a complex temperature sensitive detector; and, it is difficult to calibrate for a non-homogenous sample, e.g., paper coated with inorganic materials such as clay, calcium carbonate, or titanium dioxide. For these reasons, no further discussion is provided on the x-ray fluorescence approach.

One particular problem associated with prior art x-ray absorption measurement systems having both a single x-ray source and detector has been measuring the total mineral content in a paper web having three mineral additives such as clay, calcium carbonate and titanium dioxide. While much success has been achieved measuring total mineral content in a paper web having any two-component mineral additive mixture of clay, calcium carbonate, and titanium dioxide with a single x-ray source instrument, if a third mineral additive is used, the accuracy of measuring the total mineral content of the paper web with such a device is compromised.

One solution to the above mentioned problem is to employ a single x-ray beam with a stacked ion chamber. With a stacked ion chamber, three ion chambers are positioned one on top of the other with each chamber having a different sensitivity to the detectable mineral additives. Another solution is to employ multiple x-ray beam sources operating at different energy levels centered near detection levels for the individual mineral additives.

With regard to the later solution, the use of multiple x-ray beam sources with corresponding detectors tuned to different sensitivities of the various mineral additives is very expensive. Further, the derived outputs using multiple x-ray beam sources are subject to reduced accuracy since the variance of each source must be accounted for in the measurements. The primary source of uncertainty, or instrument variance, is in the x-ray tube and associated high voltage power supply (HVPS), as it remains exceedingly difficult to construct a stable x-ray source.

As to the former solution, using a stacked ion chamber avoids the problem from root mean square (RMS) addition of multiple sources. However, a stacked ion chamber suffers from both the difficulty of positioning the chambers to achieve maximum signal collection, due to the typical bulky size of the chambers, and the poor signal collection in the chamber furthest from the single x-ray source.

Accordingly, the current focus in the art has been to attempt to solve the above-mentioned problems. One such prior art system is described in U.S. Pat. No. 5,854,821 (the '821 patent) to Chase et al., which shows an improved x-ray measuring process for measuring mineral components, referred to as "ash", in paper having at least three such mineral components. To measure ash, the '821 patent utilizes two adjacent x-ray sources placed on one side of a paper web, and two corresponding adjacent detectors placed on the opposite side of the paper web with the first source operating at an energy level higher than the second source. It is asserted that improved composition detection for ash in paper can be achieved in this manner. However, one skilled in the art will notice that operating such a system is still subject to reduced accuracy since variance of each x-ray source must also be considered. Further, as mentioned above, the use of multiple x-ray sources is a very expensive solution to the problem.

Therefore, there is a need for a cost effective method and system to measure individual component concentrations of at least three mineral additives in a paper web in an on-line paper manufacturing process that minimizes signal attenuation.

SUMMARY OF THE INVENTION

This need is currently met by the system and method of the present application wherein a single x-ray source is utilized with a multiple filtered detection arrangement to accurately determine the total mineral content in sheet material having at least three mineral additive components and also the individual concentrations of the mineral additive components.

In accordance with one aspect of the present invention, a system is provided for determining on-line measurements of various mineral additive components, such as clay, calcium carbonate, and titanium dioxide, in a paper web or paper sheets utilizing a single x-ray source and three filtered radiation detectors. Thin filters are used to shape and/or "harden" the detected spectrum of x-rays received by each detector. Hardening refers to a specific kind of change to the radiation spectrum where only low energies are reduced or eliminated. It is to be appreciated that the type and thickness of these filters are selected to maximize sensitivity differences for the various mineral components desired to be measured by the present system.

In a preferred application of the present invention, a single x-ray source generates an x-ray beam that passes through a continuously flowing paper web in a paper manufacturing process to at least three filters on the opposite side of the web. The beam, after passing through the filters, is detected by a corresponding number of detectors. The filters cause the measurement sensitivities of the detectors to vary and hence be tuned for particular mineral additives. Accordingly, each detector generates an analog signal in response to the detected energy level of the beam. It is to be appreciated that these detectors can consist of detectors known in the art or any combination of such known detectors, for example and not limited to, solid-state detectors, ion chamber detectors, and scintillation detectors.

Due to size and cost considerations, however, solid-state detectors are preferred, and more specifically, PIN (Positive-lntrinsic-Negative) diode detectors. In the present invention, although PIN diode detectors are normally operated in the conductive (or reverse biased) mode it is preferred that the PIN diode detectors be operated in a voltaic mode. Operating the PIN diode detectors in the voltaic mode ensures that no biasing of the diode detectors is required.

In response to the analog signals generated by the detectors and additional signals from conventional basis weight and moisture sensing instruments, a processor using one of a number of know computational methods derives measurements for total mineral content and also the individual component concentrations of titanium dioxide, calcium carbonate, and day in the paper web. One known method which can be used to derive such measurements is to calibrate each detector using known concentrations of mineral additives in samples to determine base curve coefficient constants. Using the determined base curve coefficient constants together with the noted analog signals, the processor solves a multiple linear regression to determine separate measurement solutions for each mineral component. Total mineral content can then be computed as the sum of the solutions of each individual component.

In accordance with another aspect of the present invention, a method is provided for determining on-line measurements of clay, calcium carbonate, and titanium dioxide in a paper web using a filtered radiation source with multiple detectors. The method comprises the steps of determining the various mineral component concentrations in paper by first directing a broadband radiation beam emitted from a radiation source towards the paper. After passing through the paper, portions of the radiation beam are modified by three filters to define a shaped radiation spectrum that maximizes the sensitivity differences for the desired detectable mineral components. A detector is associated with each filter such that the shaped radiation spectrum for each filter falls on the corresponding detector. Signals generated by the detectors in response to the shaped radiation spectrum are sent to a processor appropriately programmed to determine the individual component concentrations of the mineral additives in the paper web.

Further features and advantages of the invention can be determined by reference to the specification and drawings which are by way of example only and not in limitation of the invention which is defined by the claims and equivalents thereto.

DETAILED DESCRIPTION OF THE INVENTION

Figure 1:
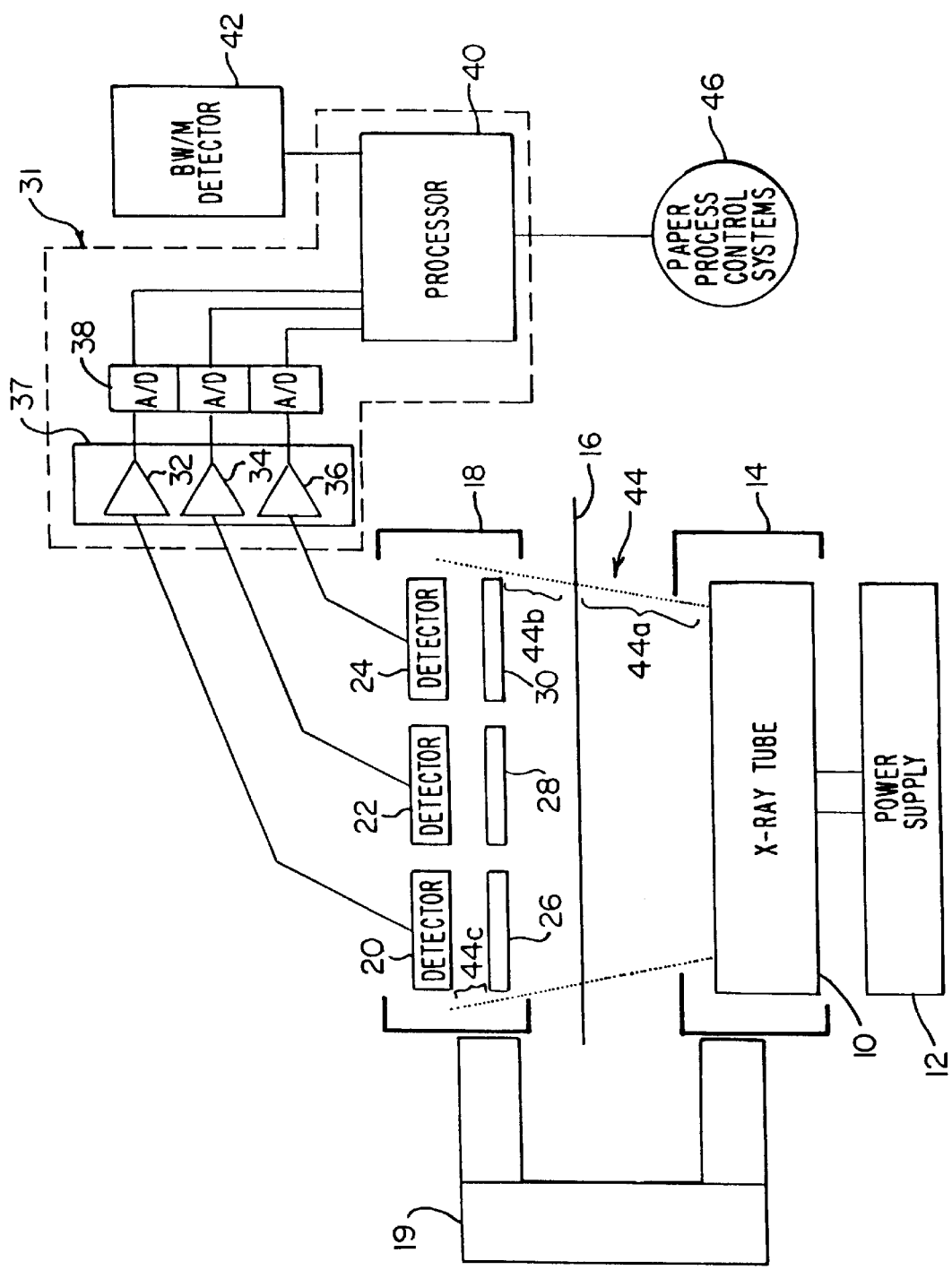
FIG. 1 is a diagram schematically illustrating a system according to a currently preferred embodiment of the present invention.

FIG. 1 shows a radiation source, preferably an x-ray tube 10 capable of emitting x-ray radiation at up to 10,000 electron volts (eV), coupled to a high-voltage power supply 12. The x-ray tube 10 is conventionally mounted within a source housing 14 on one side of a continuously advancing paper web 16 as the paper web 16 is being produced by a paper making machine (not shown). On the other side of the paper web 16 is a detector housing 18. It is to be appreciated that both the source housing 14 and the detector housing 18, as illustrated, can be mounted in a conventional scanning system 19, which moves both housings 14, 18 in synchronization across the paper web 16.

Enclosed in the detector housing 18 are three radiation detectors 20, 22, 24 each with a corresponding radiation shaping filter 26, 28, 30 associated therewith and positioned between the paper web 16 and its associated detector. If preferable, the filters 26, 28, 30 can be attached to the detectors 20, 22, 24, respectively, or alternatively, located between the paper web 16 and the x-ray tube 10, see FIG. 3. In the currently preferred embodiment, the radiation detectors 20, 22, 24 comprise solid-state detectors such as Si(Li) or Si PIN diode detectors, and for cost reasons, Si PIN diode detectors are currently preferred over the more expensive Si(Li) detectors. Since solid state radiation detectors can be manufactured in a variety of sizes and shapes, for one embodiment of the present invention, the detectors 20, 22, 24 each measured approximately 10 millimeters (mm) by 10 mm for convenient mounting in the detector housing 18. One suitable PIN diode detector is the PF-2500 room temperature detector manufactured by MOXTEK, Inc. of Orem, Utah.

It is also to be appreciated that the detectors 20, 22, 24 are operated in the voltaic mode, such that no bias is required for the detectors. Generally, radiation detectors are operated in the conductive mode but it has been found that better performance is obtained, with respect to radiation damage and temperature sensitivity, if the detectors are operated in the voltaic mode. Additionally, operating the detectors in the voltaic mode eliminates the need for a bias power supply that is required if ionization chamber detectors are used. Further, since the detectors 20, 22, 24 have the same common radiation source, i.e., the x-ray tube 10, accounting for the instabilities of different sources and power supplies is not required.

Electrically coupled to each of the detectors 20, 22, 24 is an electronic assembly 31 for processing signals representative of radiation detected by the detectors 20, 22, 24 to determine characteristics of the paper web 16. Preferably, for PIN diode detectors, the electronic assembly 31 consists of transimpedance amplifiers 32, 34 and 36, analog-to-digital (A/D) converters 38, and a processor 40. However, as known in the art, the electronic assembly 31 may vary depending on the type of detectors used. One of the transimpedance amplifiers 32, 34, 36 is used with each of the detectors 20, 22, 24 to measure the electrical potential between charged elements within each of the PIN diode detectors. The transimpedance amplifiers 32, 34, 36 comprise a single circuit 37 for simultaneous amplification of the analog signals from the detectors 20, 22, 24 as the radiation is detected. The amplified analog signals are received by the A/D converters 38, which convert the analog signals to digital signals which are passed to the processor 40. The processor 40 also receives signals from conventional detectors identified by the numeral 42 that provide information regarding the paper web 16 such as paper basis weight (BW) and moisture (M) content.

For preferred operation of the present invention, an x-ray beam having a broadband spectrum is generated by the x-ray tube 10 by a process called Bremsstrahlung, which is the electromagnetic radiation produced by acceleration of charged particles. Basically, energetic electrons from an anode impact onto a high atomic number target to produce an x-ray beam having a desired maximum energy level. It is known to one skilled in the art that various anode voltages and targets, e.g., cobalt, can be employed to produce a Bremsstrahlung spectrum of x-rays of varying maximum energies. As such, varying the voltage applied to the anode of the x-ray tube 10 modifies the energy spectrum produced by the x-ray tube 10 and hence the energy spectrum received by each of the detectors 20, 22, 24. Finding the preferred anode voltage for the x-ray tube 10 depends on the type of filters and detectors used and the type of paper web to be measured. Since a single radiation source, X-ray tube 10, is used, the selection of the anode voltage affects all the detectors 20, 22, 24. It is to be appreciated that the anode voltage can not be selected on an individual detector basis. Accordingly, the preferred anode voltage is determined by calibrating the particular system to determine which system settings give the best results to accomplish measurements of the desired detectable mineral additives in the type of paper web being measured. However, in order to tune the system more efficiently using correction factors in an instrument algorithm, explained hereafter, eliminates the difficult task of tuning the existing instruments by filter selection and high voltage adjustments.

In the present invention mineral measurements are performed using the single radiation source, the x-ray tube 10, instead of multiple radiation sources as in the prior art. FIG. 1 illustrates a first part 44a of a generated x-ray beam 44 emitted from the x-ray tube 10 towards the paper web 16. A second part 44b of the x-ray beam 44 represents the portion of the x-ray beam 44 that passes through the paper web 16 towards the filters 26, 28, 30. The type and thickness of the filters 26, 28, 30 are selected in order to maximize sensitivity differences between the detectors 20, 22, 24 for the desired detectable mineral additives. Sensitivity differences can be maximized when clay, calcium carbonate, and titanium dioxide are present in the paperweb 16 due to the unique x-ray absorption spectrum of these mineral additives.

Figure 2:
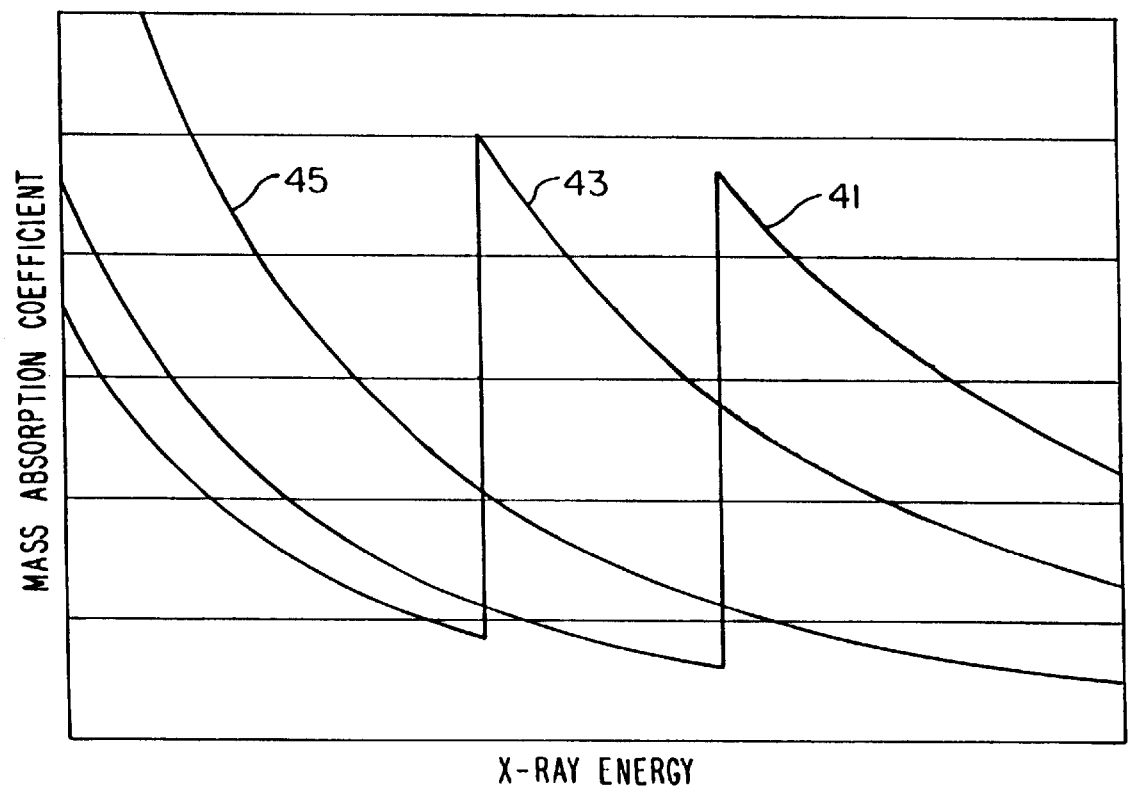
FIG. 2 is a graph showing the x-ray energy versus the mass absorption coefficient for three mineral additives of a paper web.

In particular, large discontinuities are present in the x-ray absorption spectrums for titanium dioxide and calcium carbonate due to the presence of titanium and calcium atoms in these compounds. As shown in the plot of x-ray energy vs. mass absorption coefficient ($cm^2/g$) of FIG. 2, the mineral additives of titanium dioxide, indicated by line 41, and calcium carbonate, indicated by line 43, exhibit large changes at energy levels associated with the binding energy of their respective K-shell electrons. Clay, indicated by line 45, however, does not show such absorption coefficient changes since the atoms that make up clay do not have K-shell electron binding energies within the energy band extending from 2 Kev to 10 keV. It should be understood that the graph in FIG. 2 is not intended to be of any particular scale, nor is it intended to be completely accurate. However, the important feature of the graph is that these unique differences in absorption spectrum allow the measurement sensitivity to be modified for these mineral components by changing the shape of the x-ray spectrum with the filters 26, 28, 30.

Accordingly, the thin filters 26, 28, 30 are used to shape and/or "harden" the detected spectrum of x-rays received by each detector. This is an important feature of the present invention since the filters 26, 28, 30 each shape their own portion of the energy spectrum of x-ray beam 44 falling on the detectors 20, 22, 24. However, it is to be appreciated that the filters used to modify the radiation spectrum may or may not have K, L, or M edge discontinuities in the range of 2 to 7 KeV. For example, suitable filters include aluminum, silicon, magnesium, titanium, tin and thermoplastic resins having molecular structures that contain carbon, hydrogen or oxygen. In a currently preferred embodiment, filters of thickness ranging from 3.5 $\mu$m to 25 $\mu$m are used, and more specifically, the filter 26 is formed from 25 $\mu$m aluminum, the filter 28 is formed from 25 $\mu$m titanium, and the filter 30 is a two-layer composite consisting of 3.5 $\mu$m tin and 3.5 $\mu$m titanium. Accordingly, it is a third part 44c of the x-ray beam 44 that represents the portion of the x-ray beam which has been modified as it passes through the filters 26, 28, 30 and falls on the detectors 20, 22, 24, respectively, for detection.

Upon detection of the x-ray beam 44, signals from the detectors 20, 22, 24 are generated and passed to the transimpedance amplifiers 32, 34, 36 which amplify the signals and relay the amplified signals representative of the detected energies to the A/D converters 38 for conversion to digital signals which are passed to the processor 40. As mentioned above, the transimpedance amplifiers 32, 34, 36 preferably comprise the single circuit 37 to provide separate gain channels for the detectors 20, 22, 24. The processor 40 uses data provided by the detectors 20, 22, 24 to solve for each of the components in the paper web 16, such as for ash and fiber, and of which a discussion will be provided later. The resulting component solutions can then be passed from the processor 40 to a control system/mechanism 46 for further use in the paper manufacturing process.

Figure 3:
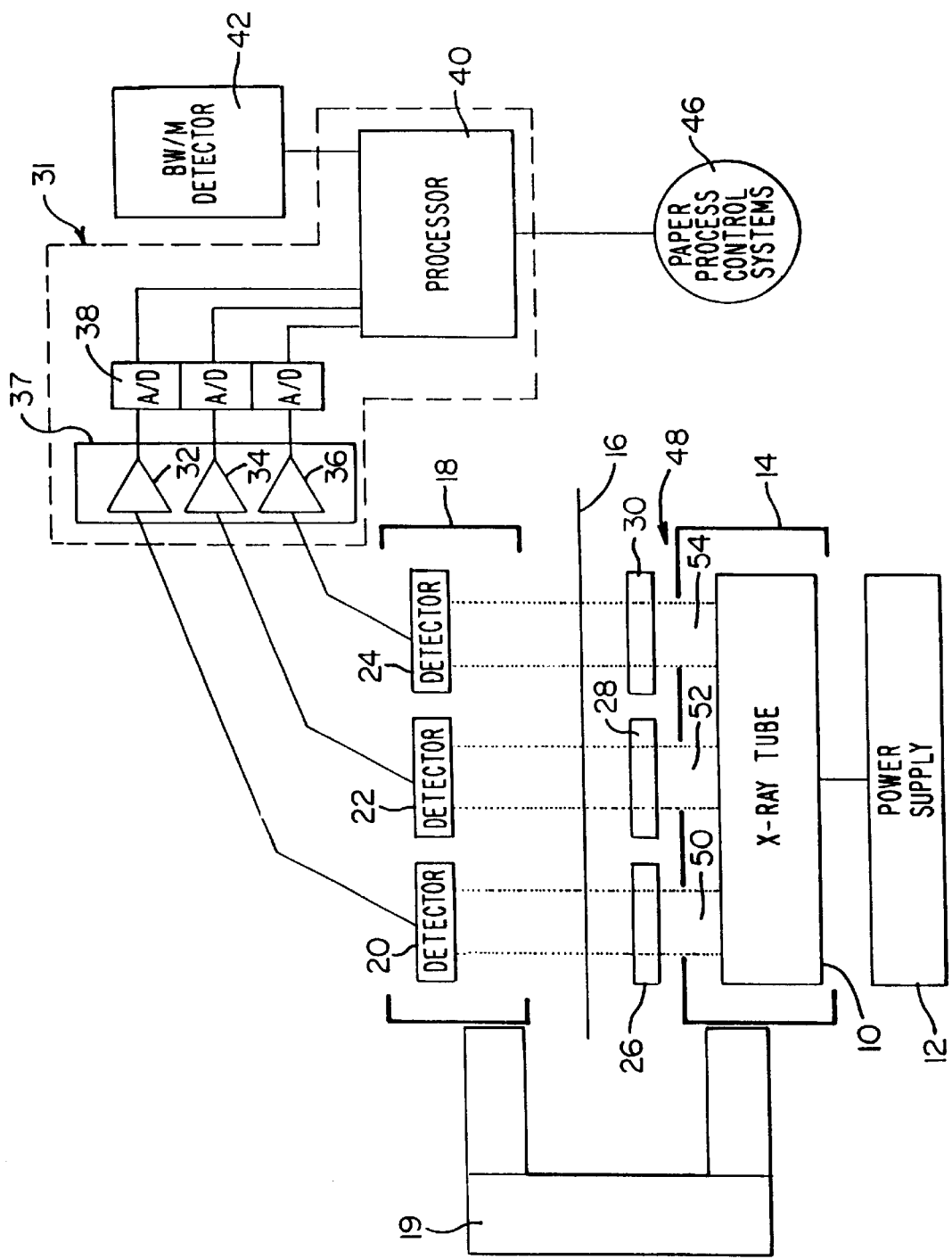
FIG. 3 is a diagram schematically illustrating a system according to an alternative embodiment of the present invention.

FIG. 3 shows an alternate embodiment of the present invention. Herein, like elements in the embodiments of FIGS. 1 and 3 will be identified using the same reference numerals. In the embodiment of FIG. 3, a beam collimator 48 having a number of exit holes or beam source apertures 50, 52, 54 equal to the number of detectors is placed between the x-ray tube 10 and the paper web 16. As shown, the collimator 48 is a portion of the source housing 14, but, if desirable, it can be a separate component. The x-ray beam emitted from the x-ray tube 10 is divided into three separate radiation beams by passage through the beam source apertures 50, 52, 54 such that separate beams emitting from the single x-ray source 10 fall on the detectors 20, 22, 24, respectively.

Also in the embodiment of FIG. 3, the filters 26, 28, 30 are located on the source side of the paper web 16, of course, the filters 26, 28, 30 can also be located on the detector side of the paper web as in FIG. 1, if desired, when the beam collimator 48 is utilized. The addition of the beam collimator 48 reduces the x/y alignment sensitivity of the x-ray tube 10 and the detectors 20, 22, 24 by forcing the separate beams to be slightly smaller than the corresponding detectors. Preferably, the beam's illumination footprint on each detector is about one millimeter smaller than the detector size. However, since the collimator allows less of x-ray beam 44 to illuminate a smaller area on each of the detectors 20, 22, 24, in this configuration, it is currently believed that the relative x/y module deflection between the x-ray tube 10 and detectors 20, 22, 24 is usually less than 1 mm.

It is noted that a number of methods can be used to solve for the total mineral additive content and the particulars of these methods form no part of the present invention. However, for the sake of example, a method for solving for the total mineral additive content and the individual component concentrations of the mineral additives in the paper web 16 will now be described. It is to be appreciated that the detectors 20, 22, 24 are infinitely thick (2–3 mm) as far as the energy of the X-ray beam 44 falling on the detector is concerned. Accordingly, all impinging photons in the X-ray beam 44 give up their energy in the detectors 20, 22, 24. However, as known, only photons with a certain level of energy are able to free electrons in the detectors from their atomic bonds to produce an electric current. This level of energy, known as the band-gap energy, is defined as the amount of energy required to dislodge an electron from its covalent bond and allow it to become part of an electrical circuit. The energy that photons possess is called the photon energy. This photon energy must be at least as high as the band-gap energy for a photon to free an electron. As such, when a photon with sufficient energy strikes any of the detectors 20, 22, 24, it promotes an electron from the valence band (filled orbitals) to the conduction band (unfilled orbitals) creating an electron(−)—hole(+) pair. Equation (1) shows that for an incident photon of energy (E) on a detector with a band-gap energy (Eg), N electron-hole pairs are created:

$$N=E/Eg \quad (1)$$

Since PIN detectors 20, 22, 24 contain a p-n junction, the electron-hole pairs separate producing a potential difference, which can be measured, that forces current to flow in an external circuit. The current can be calculated at energy increment (E) in each detector as:

$$A(E)=(E/Eg)*Hz/eV(E)*1.6*10^{-19} \quad (2)$$

where:

A(E)=Amperes/eV at a photon energy of (E)

E/Eg=(N) in Equation 1 at photon energy (E)

Hz/eV(E)=the count rate at photon energy (E)

$1.6*10^{-19}$=the fundamental electron charge, in coulombs (1 Ampere=1 Coulomb per second).

To calculate total detector current (Ic), each energy increment between zero and Emax, the maximum kinetic energy radiated by the x-ray source 10, is numerically summed, as shown in Equation 3:

$$Ic = \sum_{E=0}^{Emax} A(E) = \text{Total Amperes} \quad (3)$$

To evaluate the influence of X-ray filtering on the detectors response to the desired detectable mineral components an effective instrument mass attenuation coefficient for each component is calculated.

Each detector is calibrated using a series of known concentrations of mineral additives in samples to determine a unique calibration set of mass attenuation coefficients for each detector. It is to be appreciated that the coefficients are derived from a plot of the analytical signal (the detector response) as a function of material concentration that is obtained from measuring the signal from the series of standards of known concentrations. These coefficients are then used to linearly tune the system in order to determine the concentration of an unknown sample. It is to be appreciated that calibrating the system with coefficients eliminates the need to carry out the difficult task of tuning the existing instruments by filter selection and high voltage adjustments.

In performing the calibration of the detectors, incremental changes in each component (including cellulose and water) are made in order to compute the effective instrument mass attenuation coefficients. The detector response is calculated as shown in Equations (2) and (3).

Once the mass attenuation coefficient spectrum for the components in the paper web are known, it is relatively simple to calculate the amount of electromagnetic energy transmitted through the paper web using the basic relationship:

$$I=I_0 * e^{-\mu_f x_f - \mu_a x_a - \mu_w x_w} \quad (4)$$

where:

I = the transmitted energy through the substance,
$I_0$ = the incident energy on the substance,
$\mu_f$ = the mass attenuation coefficient for fiber in units of cm²/g for a particular energy,
$X_f$ = the area weight of fiber in g/cm²,
$\mu_a$ = the mass attenuation coefficient for mineral in units of cm²/g for a particular energy,
$X_a$ = the area weight of mineral in g/cm²,
$\mu_w$ = the mass attenuation coefficient for water in units of cm²/g for a particular energy, and
$X_w$ = the area weight of water in g/cm².

Equation (3) can be re-written as:

$$Ln(T)/BWT=-\mu_f F_f - \mu_a F_a - \mu_w f_w \quad (5)$$

where:

BWT = basis weight (sum of fiber weight, mineral weight, water weight) per unit of area,
Ln(T) = $I/I_0$, the ratio of the detected response in the presence of paper to the detected response in the absence of the paper,
$F_f$ = fiber fraction (fiber weight divided by base weight)
$F_a$ = mineral fraction (mineral weight divided by base weight), and
$F_w$ = water fraction (water weight divided by base weight).

As mentioned above, BWT and water weight are provided by conventional detectors 42. Accordingly, equation (5) is a simplified expression that shows approximately how signals from individual detectors behave. Placing selected filters over the detectors makes the mass attenuation coefficients for mineral components and for fiber different. By measuring a set of laboratory standard samples having no mineral components and samples having varying amounts and types of mineral components and using the resulting data in the expression of equation (4), the mass attenuation coefficients for a mineral component and fiber can be calculated for each detector.

In solving for the total and individual mineral contents, the calibration set of mass attenuation coefficients, along with signal responses from the detectors 20, 22, 24 are plugged into a linear equation that represents each component. For the detectors 20, 22, 24, a calibration set of mass attenuation coefficients K0$x$, K1$x$, K2$x$, K3$x$, where x stands for the particular detector, when applied to the logarithm of each signal (X), generates a first calibrated response of "base curve" coefficient constants $BWM_1$, $BWM_2$, $BWM_3$, one for each of the detectors 20, 22, 24. This set of "base curve" coefficient constants is determined from calibration readings conducted on Mylar samples with each of the detectors 20, 22, 24 using the following formula:

$$BWM = X/(K0 + K1*X + K2*X^2 + K3*X^3) \qquad (6)$$

where:

BWM=Basis Weight Mylar;

X=In(T), the sum of the known mass attenuation coefficients times the known weight of each component (mineral, fiber and water) from an array of Mylar calibration samples;

K0, K1, K2, K3=the "base curve" coefficient constants generated from reading the array of Mylar calibration samples with each solid-state detector.

It is to be appreciated that using a calibration set of "base curve" coefficient constants simplifies the mineral equation as the form of the present equation recognizes that the detected signal is not a simple exponential function versus process weight. Accordingly, the high order coefficient constants K1, K2 and K3 are used to compensate for the fact that attenuation is not a simple exponential, as was indicated in equation (4) and (5). As such, equation (6) makes the instrument response substantially linear in weight, for each detector, thus reducing the instrument algorithm to simple multiple linear regression equations consisting of five coefficients for the measured terms, $BWM_1$, $BWM_2$, $BWM_3$, basis weight (BW) and moisture weight (WW) and, if necessary, an offset coefficient used to provide for a best fit. For instance, the solutions for titanium dioxide (T), calcium carbonate (K), and clay (C) using twelve different coefficients has the form:

$$T = A_T*BWM_1 + B_T*BWM_2 + C_T*BWM_3 + D_T*BW + E_T*WW$$

$$K = A_K*BWM_1 + B_K*BWM_2 + C_K*BWM_3 + D_K*BW + E_K*WW$$

$$C = A_C*BWM_1 + B_C*BWM_2 + C_C*BWM_3 + D_C*BW + E_C*WW$$

where $A_{(T,K,C)}$, $B_{(T,K,C)}$, $C_{(T,K,C)}$, $D_{(T,K,C)}$, $E_{(T,K,C)}$ are the solved-for unknown coefficients. Accordingly, total mineral weight can be computed as the sum of the solutions of each individual component. By conducting multiple linear regressions on these linear equations, solving for the remaining unknown coefficients in the equation will determine the separate concentration measurements for each mineral component. Further, in the solutions for titanium dioxide, calcium carbonate and clay, only a multiple linear relationship is shown. It is possible to improve the correlation by using higher order terms of $BWM_x$ and cross-relation terms like $BWM_x*BWM_y$. Using neural networks process modeling tools (such as "Process Insights" from Pavilion Technologies, Inc., Austin, Tex.) these non-linear relationships can be explored and the prediction for the true amounts of mineral constituents may be improved. Moreover, it should be understood that the system arrangement and resulting coefficient constants are not intended to be limitations of the present invention but as an example of the principles disclosed herein, as it is obvious to one skilled in the art that other x-ray filters and/or other high voltages may cause different results.

For solution methods for total mineral additive content, U.S. Pat. No. 5,854,821, which is incorporated herein by reference, can also be consulted.

Having thus described the methods and apparatus of the present invention in detail and by reference to preferred embodiments thereof, it will be apparent that modifications and variations are possible without departing from the scope of the invention detailed in the appended claims.

What is claimed is:

1. A method of determining concentrations of mineral components comprising the steps of:

directing a X-ray beam emitted from a X-ray source into a material including mineral components;

filtering at least three portions of said X-ray beam with a corresponding number of filters;

positioning detectors to individually receive said filtered portions of said X-ray beam; and determining concentrations of said mineral components in said material from output signals of said detectors in response to said filter portions of said X-ray beam.

2. A method of determining concentrations of mineral components as claimed in claim 1 further comprising the step of selecting the type and thickness of said filters in order to increase sensitivity differences between said detectors for said mineral components.

3. A method of determining concentrations of mineral components as claimed in claim 1 further comprising the step of supporting said X-ray source in a source housing.

4. A method of determining concentrations of mineral components as claimed in claim 1 further comprising the steps of:

forming said filters from one or more materials selected from a group consisting of aluminum, silicon, magnesium, titanium, tin and thermoplastic resins having molecular structures that contain carbon, hydrogen or oxygen; and forming each of said filters to have a desired thickness ranging from 3.5 $\mu$m to 50 $\mu$m.

5. A method of determining concentrations of mineral components as claimed in claim 1 further comprising the step of supporting said filters and said detectors in a detector housing.

6. A method of determining concentrations of mineral components as claimed in claim 5 wherein said material comprises a paper web being manufactured and said method further comprises the steps of:

supporting a source housing containing said X-ray source on a first side of said paper web;

supporting said detector housing on a second side of said paper web; and scanning said source housing and said detector housing across said paper web.

7. A method of determining concentrations of mineral components as claimed in claim 1 further comprising the step of supporting said filters and said source in a source housing.

8. A method of determining concentrations of mineral components as claimed in claim 7 wherein said material comprises a paper web being manufactured and said method further comprises the steps of:

supporting a source housing containing said X-ray source on a first side of said paper web;

supporting said detector housing on a second side of said paper web; and scanning said source housing and said detector housing across said paper web.

9. A method of determining concentrations of mineral components as claimed in claim 1 further comprising the step of providing a collimator that defines at least three beam source apertures through which said X-ray beam is emitted.

10. A method of determining concentrations of mineral components as claimed in claim 1 further comprising the step of providing an electronic circuit associated with said detectors for processing signals representative of X-rays detected by said detectors to determine characteristics of said material.

11. A method of determining concentrations of mineral components as claimed in claim 10 further comprising a step of providing the signals representative of X-rays associated with said detectors to a processor.

12. A system for determining concentrations of mineral components comprising:
- a single X-ray source for emitting a X-ray beam into a material including mineral components;
- at least three filters to filter said X-ray beam;
- at least three detectors for receiving said filtered X-ray beam; and
- a processing assembly electrically coupled to said detectors for determining concentrations of said mineral components from signals generated by said detectors in response to said filtered X-ray beam.

13. A system for determining concentrations of mineral components as claimed in claim 12 wherein said at least three filters are located on a detector side of said material.

14. A system for determining concentrations of mineral components as claimed in claim 12 wherein said at least three filters are located on a X-ray source side of said material.

15. A system for determining concentrations of mineral components as claimed in claim 12 wherein said X-ray source produces a X-ray beam by the process of Bremsstrahlung.

16. A system for determining concentrations of mineral components as claimed in claim 12 further comprising a source housing for supporting said X-ray source.

17. A system for determining concentrations of mineral components as claimed in claim 12 wherein said at least three filters each comprise at least one component selected from a group consisting of aluminum, silicon, magnesium, titanium, tin and thermoplastic resins having molecular structures that contain carbon, hydrogen or oxygen.

18. A system for determining concentrations of mineral components as claimed in claim 12 wherein said at least three filters are of a desired thickness ranging from approximately 3.5 $\mu$m to 50 $\mu$m.

19. A system for determining concentrations of mineral components as claimed in claim 12 wherein each of said detectors is a detector selected from a group consisting of ion chambers, PIN diodes, and scintillation detectors.

20. A system for determining concentrations of mineral components as claimed in claim 12 further comprising of a detector housing for supporting said at least three filters and said at least three detectors.

21. A system for determining concentrations of mineral components as claimed in claim 20 further comprising a conventional scanning system, and a source housing that supports said X-ray source, wherein said detector housing and said source housing are mounted on said conventional scanning system so that said source housing and said detector housing are movable in synchronization across a paper web.

22. A system for determining concentrations of mineral components as claimed in claim 12 wherein said source housing comprises a collimator assembly that defines at least three beam source apertures through which said X-ray beam is emitted.

23. A system for determining concentrations of mineral components as claimed in claim 12 wherein said signals generated by said detectors are analog and said processing means includes a transimpedance amplifier electrically associated with each of said detectors for amplifying said analog signals and A/D converters to convert said analog signals to digital signals which are passed to said processor.

24. A system for determining various mineral component concentrations in a paper web as claimed in claim 22 wherein said processing assembly is comprised of an analog-to-digital converter electrically coupled to each electrometer for converting the analog signals to digital signals representative of X-rays detected by said detectors, and a processor electrically coupled to said analog-to-digital converter for receiving said digitally converted analog signals from said detector, said processor is capable of determining concentrations of said mineral components from said signals.

25. A method of determining concentrations of mineral components comprising the steps of:
- directing a X-ray beam emitted from a single X-ray source into a material including mineral components;
- shaping said X-ray beam before passing through said material with at least three filters to define separate potions of said X-ray beam with a defined X-ray spectrum in each portion of said X-ray beam;
- positioning detectors to individually receive said shaped portions of said X-ray beam from said at least three filters after passing through said material; and
- determining concentrations of said various mineral components in said material from the outputs of said detectors in response to said shaped portions of said X-ray beam.

26. A method of determining concentrations of mineral components as claimed in claim 25 further comprising the step of providing a collimator that defines at least three beam source apertures through which said X-ray beam is emitted.

* * * * *

UNITED STATES PATENT AND TRADEMARK OFFICE
CERTIFICATE OF CORRECTION

PATENT NO. : 6,377,652 B1  
DATED : April 23, 2002  
INVENTOR(S) : Steven Perry Sturm It is certified that error appears in the above-identified patent and that said Letters Patent is hereby corrected as shown below:

<u>Title page,</u>  
Item [57], ABSTRACT,  
Line 4, "are cover" should read -- are covered --.

<u>Column 1,</u>  
Line 12, "manufactures" should read -- manufacturers --.

<u>Column 3,</u>  
Line 36, "know computational" should read -- known computational --.  
Line 39, "and day" should read -- and clay --.

<u>Column 5,</u>  
Line 60, "paperweb" should read -- paper web --.  
Line 7, "2 Kev to 10 ke V" should read -- 2 KeV to 10 KeV --.

<u>Column 8,</u>  
Line 24, "$I = I_0 * e^{-\mu_f x_f - \mu_a - \mu_w x_w}$" should read -- $I = I_0 * e^{-\mu_f x_f - \mu_a x_a - \mu_w x_w}$ --.

Line 38, "Ln(T)/BWT = $-\mu_f F_f - \mu_a F_a - \mu w F w$" should read  
-- Ln(T)/BWT = $-\mu_f F_f - \mu_a F_a - \mu_w F_w$ --.

<u>Column 11,</u>  
Line 55, "comprising of a" should read -- comprising a --.

<u>Column 12,</u>  
Line 40, "potions" should read -- portions --.

Signed and Sealed this

Sixth Day of May, 2003

JAMES E. ROGAN  
*Director of the United States Patent and Trademark Office*

UNITED STATES PATENT AND TRADEMARK OFFICE
CERTIFICATE OF CORRECTION

PATENT NO. : 6,377,652 B1
DATED : April 23, 2002
INVENTOR(S) : Steven Perry Sturm It is certified that error appears in the above-identified patent and that said Letters Patent is hereby corrected as shown below:

Title page,
Item [57], ABSTRACT,
Line 4, "are cover" should read -- are covered --.

Column 1,
Line 12, "manufactures" should read -- manufacturers --.

Column 3,
Line 36, "know computational" should read -- known computational --.
Line 39, "and day" should read -- and clay --.

Column 5,
Line 60, "paperweb" should read -- paper web --.

Column 6,
Line 7, "2 Kev to 10 ke V" should read -- 2 KeV to 10 KeV --.

Column 8,
Line 24, "$I = I_0 * e^{-\mu_f x_f - \mu_a - \mu_w x_w}$" should read -- $I = I_0 * e^{-\mu_f x_f - \mu_a x_a - \mu_w x_w}$ --.
Line 38, "$Ln(T)/BWT = -\mu_f F_f - \mu_a F_a - \mu wFw$" should read
-- $Ln(T)/BWT = -\mu_f F_f - \mu_a F_a - \mu_w F_w$ --.

Column 11,
Line 55, "comprising of a" should read -- comprising a --.

UNITED STATES PATENT AND TRADEMARK OFFICE
CERTIFICATE OF CORRECTION

PATENT NO. : 6,377,652 B1
DATED : April 23, 2002
INVENTOR(S) : Steven Perry Sturm It is certified that error appears in the above-identified patent and that said Letters Patent is hereby corrected as shown below:

Column 12,
Line 40, "potions" should read -- portions --.

This certificate supersedes Certificate of Correction issued May 6, 2003.

Signed and Sealed this

Twenty-second Day of July, 2003

JAMES E. ROGAN
*Director of the United States Patent and Trademark Office*